(12) United States Patent
Olsson et al.

(10) Patent No.: US 9,863,929 B2
(45) Date of Patent: Jan. 9, 2018

(54) METHOD AND DEVICE FOR EVALUATING A WOODEN BOARD

(71) Applicant: INNOVATIV VISION AB, Linköping (SE)

(72) Inventors: Anders Olsson, Växjö (SE); Erik Serrano, Lund (SE); Jan Oscarsson, Växjö (SE); Bertil Enquist, Göteborg (SE); Marie Johansson, Växjö (SE); Bo Källsner, Täby (SE)

(73) Assignee: WOODEYE AB (SE)

( * ) Notice: Subject to any disclaimer, the term of this patent is extended or adjusted under 35 U.S.C. 154(b) by 554 days.

(21) Appl. No.: 14/383,495

(22) PCT Filed: Mar. 7, 2013

(86) PCT No.: PCT/EP2013/054586
§ 371 (c)(1),
(2) Date: Sep. 5, 2014

(87) PCT Pub. No.: WO2013/131999
PCT Pub. Date: Sep. 12, 2013

(65) Prior Publication Data
US 2015/0057954 A1    Feb. 26, 2015

(30) Foreign Application Priority Data
Mar. 8, 2012 (SE) ...................................... 1250214

(51) Int. Cl.
*G01N 33/46* (2006.01)
*G01N 21/898* (2006.01)
*G01N 3/02* (2006.01)

(52) U.S. Cl.
CPC ............... *G01N 33/46* (2013.01); *G01N 3/02* (2013.01); *G01N 21/8986* (2013.01); *G01N 2201/06113* (2013.01); *G01N 2201/105* (2013.01)

(58) Field of Classification Search
CPC .... G01N 33/46; G01N 3/02; G01N 2201/105; G01N 21/8986; G01N 2201/06113
See application file for complete search history.

(56) References Cited

U.S. PATENT DOCUMENTS 4,926,350 A    5/1990  Bechtel et al.
5,888,620 A *  3/1999  Grenier .................... B07C 5/14
                                                          144/332

(Continued)

FOREIGN PATENT DOCUMENTS

WO    WO 2011/007374    1/2011

OTHER PUBLICATIONS

Simon Aicher et al., "Determination of Local and Global Modulus of Elasticity in Wooden Boards", Otto Graf Journal, vol. 13, Jan. 1, 2002, pp. 183-198.

*Primary Examiner* — Aditya Bhat
(74) *Attorney, Agent, or Firm* — Condo Roccia Koptiw LLP

(57) ABSTRACT

The present disclosure relates to a method and device for evaluating a wooden board with an elongated direction. Data indicating fiber orientation over the surface of the board is acquired and for a number of board sub-portions a nominal local modulus of elasticity, MOE, is determined based on the fiber orientation data and a nominal material parameter. A nominal global MOE in the elongated direction for the wooden board as a whole is generated and compared with a secondary global MOE. Based on the fiber orientation data and this comparison an estimated local modulus of elasticity, MOE, in said elongated direction is generated for a number (Continued)

of board sub-portions. This data may be used e.g. for reliable strength grading of wooden boards.

17 Claims, 4 Drawing Sheets

(56) References Cited

U.S. PATENT DOCUMENTS

| | | | | |
|---|---|---|---|---|
| 6,025,053 | A * | 2/2000 | Grenier | B07C 5/14 144/332 |
| 6,276,209 | B1 * | 8/2001 | Schafer | G01N 29/07 73/597 |
| 7,047,156 | B1 * | 5/2006 | Bechtel | G01N 3/20 238/169 |
| 7,418,866 | B2 * | 9/2008 | Wang | G01N 29/07 73/597 |
| 7,680,304 | B2 * | 3/2010 | Biernacki | G01N 33/46 382/108 |
| 8,780,360 | B2 * | 7/2014 | Giudiceandrea | G01N 21/23 356/614 |

* cited by examiner

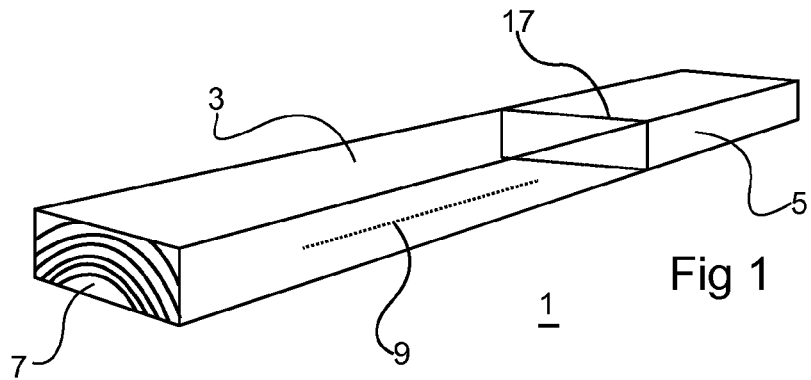
Fig 1
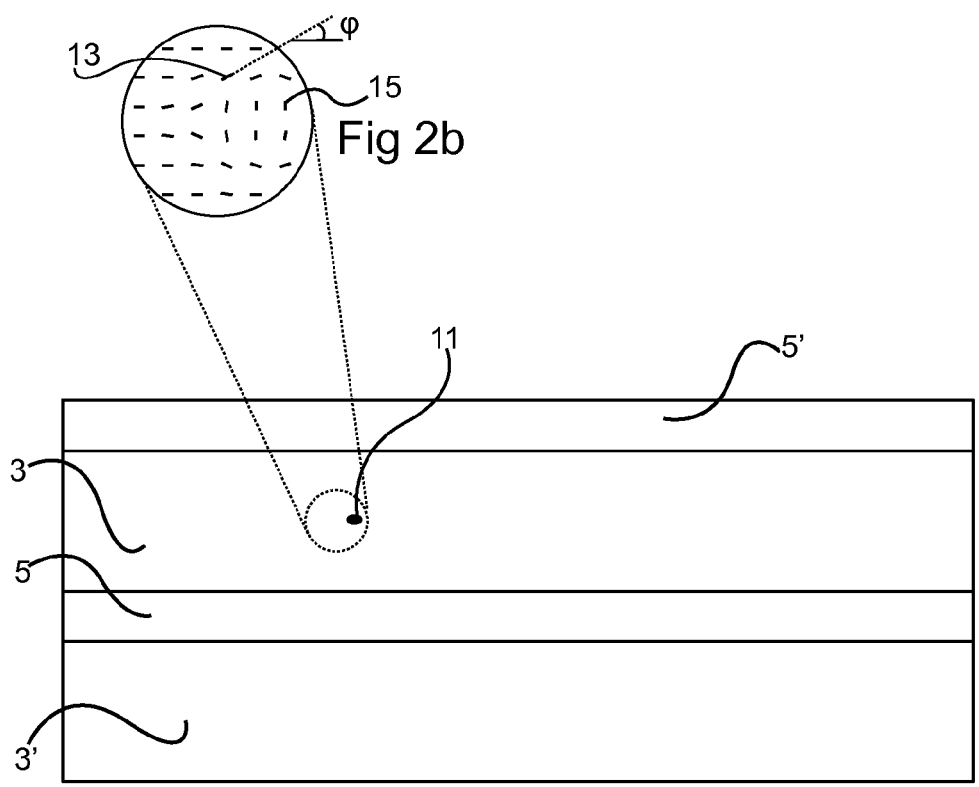
Fig 2b
Fig 2a

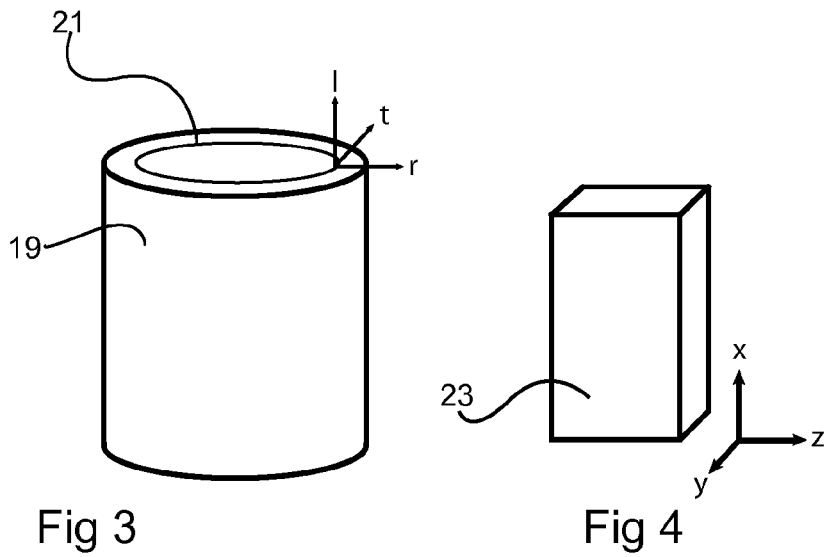
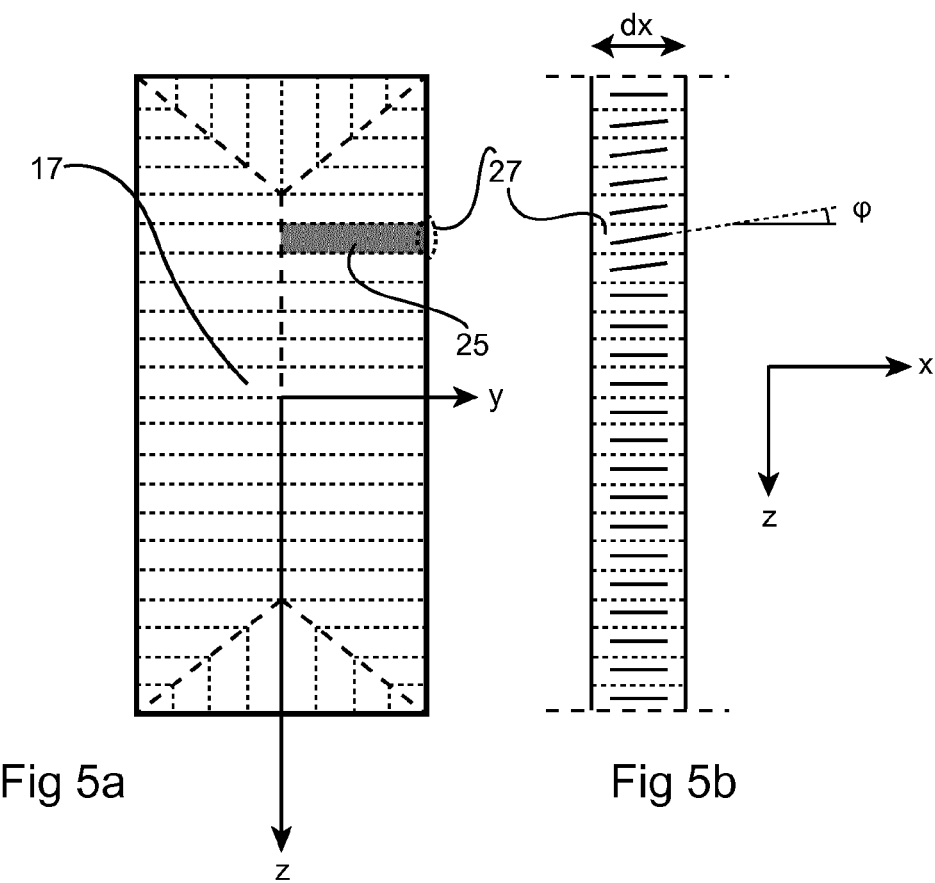

METHOD AND DEVICE FOR EVALUATING A WOODEN BOARD

This application is the National Stage Entry under 35 U.S.C. §371 of PCT Application No. PCT/EP2013/054586, filed Mar. 7, 2013, which claims the benefit of Swedish Patent Application No. 1250214-2, filed Mar. 8, 2012, the contents of each of which are hereby incorporated by reference in their entirety.

TECHNICAL FIELD

The present disclosure relates to a method and a device for evaluating a wooden board, having an elongated direction, wherein the method comprises acquiring data indicating fiber orientation over the surface of the board.

BACKGROUND

Such a method and device is disclosed in U.S. Pat. No. 4,926,350, where information about fiber orientation is obtained using the feature of a wood surface that the dielectric constant is different over a wood surface along and across a fiber direction thereof. When a wood surface is introduced between a pair of capacitor plates, the wood becomes part of the resulting capacitor, the capacitance of which can be determined using a radio frequency signal. By changing the orientation of the capacitor plates, a maximum or minimum can be found, revealing the orientation of wood fibers at that location of the board.

This information can be used to detect knots or to estimate the strength of the board.

One issue associated with the above mentioned disclosure is how to further improve board evaluation, e.g. to provide an improved strength grading method.

SUMMARY

One object of the present disclosure is therefore to obtain a method for improved board evaluation. This object is achieved by means of a method according to claim 1, and a device according to claim 11.

More specifically, the method for evaluating a wooden board, having an elongated direction, comprises acquiring data indicating fiber orientation over the surface of the board, and obtaining a secondary global modulus of elasticity, MOE, for the board as a whole. Based on the fiber orientation data and the global MOE, an estimated local modulus of elasticity, MOE, in said elongated direction is generated for a number of board sub-portions.

This provides an estimate for the local MOE that is comparatively reliable, since it is determined on the basis of both the local fiber angle and a secondary global measure. Thereby, a local MOE is adjusted depending on whether the board is cut out from a log close to or distant from the pith, for instance. The result is a substantially more reliable evaluation.

Further, to determine the estimated local MOE, a nominal local MOE in the elongated direction may be determined, for each of a number of board sub-portions, based on the fiber orientation data and at least one nominal material parameter. Based on the determined nominal local MOEs, a nominal global MOE in the elongated direction for the wooden board as a whole may be generated and compared with the secondary global MOE. The nominal local MOE may be adjusted based on the result of this comparison to obtain the estimated local MOE.

The secondary global MOE may be obtained by exciting the board with an impact in its longitudinal direction and measuring its primary resonance frequency, and the data indicating fiber orientation over the surface of the board may be acquired using a laser scanner.

The determining of a nominal local MOE in the elongated direction may be based on the assumption that a volume of wood beneath a portion of the board surface has the same fiber orientation as the portion of the surface in question.

The generated estimated local MOE may be used to strength grade the board by providing an indicating property, IP. The IP may be based on the calculated bending or axial stiffness in a number of cross sections along the board length. For instance, the minimum cross section bending or axial stiffness may be used as a basis for the IP.

The generated estimated local MOE may be used to calculate the bending or axial stiffness in a number of cross sections along the board length, which may be used also for other purposes than strength grading.

The present disclosure also relates to a device capable of carrying out the above-indicated method. The device generally involves means for carrying out the relevant steps.

BRIEF DESCRIPTION OF THE DRAWINGS

FIG. 1 shows a wooden board.

FIG. 2a illustrates an optically recorded data set indicating fiber angles over the surface of the board in FIG. 1, and FIG. 2b is an enlarged portion of FIG. 2a where individual fiber angle recordings are visible.

FIGS. 3 and 4 illustrate coordinate systems used for definition of material parameters in a log and in a board, respectively.

FIGS. 5a and 5b illustrate how surface fiber orientation data can be used to estimate bending stiffness in a board cross section.

DETAILED DESCRIPTION

Figure 6:
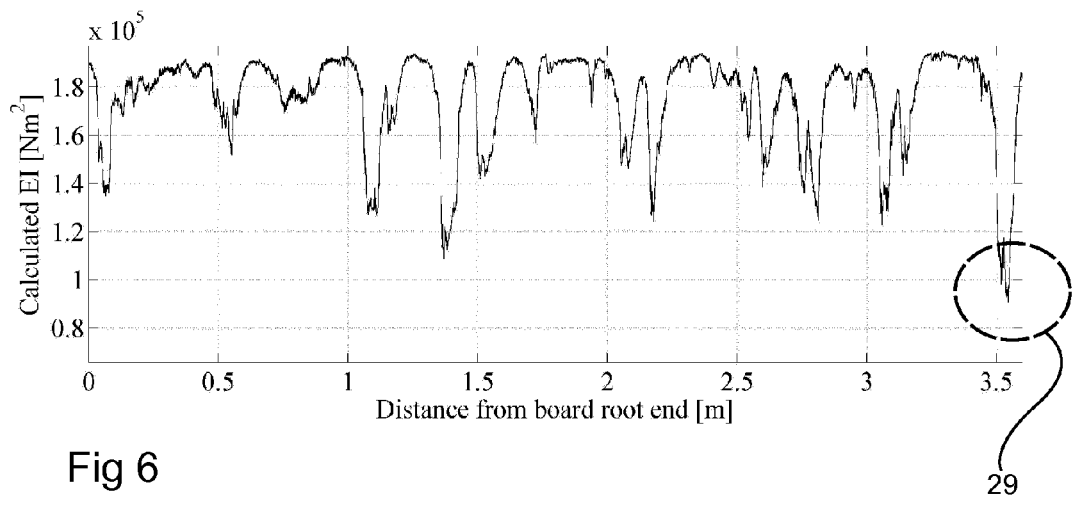
FIG. 6 shows a graph illustrating variation of cross sectional bending stiffness along a board.

The present disclosure relates to the evaluating of wood, such as wooden boards, and is useful for instance to predict the bending strength of a board, although other applications are possible. Such predicting is a process of great importance in terms of economic value.

At sawmills, produced wooden boards, intended for construction, are graded into different strength classes, such as C16, C18, etc., in correspondence with their predicted bending strength, stiffness and density. For instance, C16 implies that the bending strength of a board 1, see FIG. 1, is 16 MPa. Thus, a strength class is designated by a number that indicates the value of bending strength, for instance when the board is used as a structural beam.

Sawmills thus grade their products into different classes in accordance with a predictive measure, and the higher the class, the higher the value of the product. In accordance with standards, a certain degree of uncertainty is allowed in the prediction, typically 5% of the products graded into a class are allowed to be sub-standard, i.e. do not have the bending stiffness they are graded to have when being tested in an actual strength test.

One known way of strength grading of wooden boards is to mechanically flatwise bend (across an axis parallel with the face surface) a board over a short span of about 1 meter. This gives some indication of how the stiffness varies along the board and can be used to provide a predictive indicator for how the board is to be graded. However, this measure does not include precise information of the edgewise stiffness which is more relevant for structural applications than the corresponding flatwise stiffness.

Wood is a highly orthotropic material, meaning that its stiffness is much higher in the direction of wood fibers than across that direction. As an example the value of the modulus of elasticity (Young's modulus), hereinafter MOE, may be 10700 MPa in the fibre direction of Norway spruce, whereas it may be 710 MPa across an annual ring and 430 MPa along an annual ring.

Ideally, all fibers in a board would be oriented in a direction 9 that is parallel with the longitudinal direction of the board. This is however only the case partially and approximately within a board. Trees have branches and thus boards have knots, and around and in knots the fiber directions deviate substantially from the longitudinal direction of the board. Further, other local imperfections exist, and the board as a whole may have been sawn in a direction that deviates slightly from the fiber direction in the used timber. The growth of the tree may add further imperfections, e.g. spiralling fibres.

The present disclosure involves estimating the local stiffness of a wooden board based on actual measuring of fiber/grain orientation compared to the longitudinal direction of the board.

Already the aforementioned U.S. Pat. No. 4,926,350 discussed methods for electrically detecting the fiber orientation over the surface of a wooden board.

In the present disclosure however, the WoodEye® system is used. This system may include four sensor cameras as well as a number of lasers illuminating the board. Boards may be automatically fed through the system which simultaneously generates optical data useful to determine fibre orientation over the surface of the board. The system utilises the so-called tracheid effect to obtain this data. The result of this effect is that a circular laser dot illuminating a piece of the board will appear elliptical with the main axis of the ellips coinciding with the fibre angle in that piece. Other useful optical systems exist.

The limitations of such a system are that it only registers the fiber orientation at the surface of the board and that it does not directly detect the diving angle, i.e. the angle between the fibre and the plane of the illuminated surface. It is appreciated that other fiber orientation detection methods may be conceivable that could obtain information also about diving angles and orientation of fibers embedded under the board surface. Such additional information would possibly improve the accuracy of the analysis but this would be obtained at a much higher cost and the information available using the above-mentioned system already gives very good results. In any case, it is evident from the following description of the invention how more detailed knowledge about the three dimensional fibre orientation in the entire volume of the board would be utilized if available.

FIG. 2a illustrates an optically recorded data set indicating fiber angles over the surface of the board in FIG. 1. Data is thus recorded for the face surface 3 and the edge surface 5 in FIG. 1. Further, data is recorded for the face surface 3' and the edge surface 5' that are hidden in FIG. 1.

FIG. 2b is an enlarged portion of FIG. 2a, around a knot 11, where individual fiber angle recordings are visible. For a number of dots 13 over the board surface, angles φ are thus recorded. Typically, for an 4.8. meters long board with the dimensions 45×145 mm and scanned at a feeding speed of 400 m/min, about 70000 dots are recorded. For some locations 15 the value of the recorded fibre angle is more or less a random variable, typically within knots where the fibres are oriented almost perpendicularly through the plane of the board surface.

FIGS. 3 and 4 illustrate coordinate systems used for definition of material parameters. FIG. 3 illustrates a part of a log 19 with an annual ring 21. The wood fibre has a longitudinal extension axis, l (in ideal wood coinciding with the longitudinal direction of the log), and orthogonal axes across, r, and tangential with, t, the annual ring 21 of the log or branch of which it is a part. Thus the l-, r- and t axes have different directions in different locations of the log.

When sawn into a rectangular parallelepiped 23, as illustrated in FIG. 4, the resulting product, herein referred to as a wooden board, is instead defined in a coordinate system x, y, z, as determined by the board surfaces planes, each having one of the latter coordinate systems axes as its normal vector.

A transformation between the two coordinate systems can be made as follows. Assuming that (l,r,t) and (i,j,k) are the unit vectors along the l-r-t system and the x-y-z system, respectively, one can write $$\begin{bmatrix} l \\ r \\ t \end{bmatrix} = A^T \begin{bmatrix} i \\ j \\ k \end{bmatrix} \quad (1)$$

where $$A = \begin{bmatrix} a_l^x & a_r^x & a_t^x \\ a_l^y & a_r^y & a_t^y \\ a_l^z & a_r^z & a_t^z \end{bmatrix} \quad (2)$$

in which $a_l^x$, for instance, denotes cosine for the angle between the l- and x axes.

The wood material properties relating to the l-r-t directions can be stored in the compliance matrix $\overline{C}$ as $$\overline{C} = \begin{bmatrix} \frac{1}{E_l} & -\frac{v_{rl}}{E_r} & -\frac{v_{tl}}{E_t} & 0 & 0 & 0 \\ -\frac{v_{lr}}{E_l} & \frac{1}{E_r} & -\frac{v_{tr}}{E_t} & 0 & 0 & 0 \\ -\frac{v_{lt}}{E_l} & -\frac{v_{rt}}{E_r} & \frac{1}{E_t} & 0 & 0 & 0 \\ 0 & 0 & 0 & \frac{1}{G_{lr}} & 0 & 0 \\ 0 & 0 & 0 & 0 & \frac{1}{G_{lt}} & 0 \\ 0 & 0 & 0 & 0 & 0 & \frac{1}{G_{rt}} \end{bmatrix} \quad (3)$$

in which $E_l$, $E_r$, $E_t$ are the moduli of elasticity in the orthotropic directions, $G_{lr}$, $G_{lt}$, $G_{rt}$ are the shear moduli in the respective orthotropic planes, and the parameters $v_{lr}$, $v_{rl}$, $v_{lt}$, $v_{tl}$, $v_{rt}$ and $v_{tr}$ are Poisson's ratios. The relations $v_{rl}=E_r/E_l \times v_{lr}$, $v_{tl}=E_t/E_l \times v_{lt}$ and $v_{tr}=E_t/E_r \times v_{rt}$ hold which means that $\overline{C}$ only contains nine independent material parameters.

The material matrix $\overline{D}=\overline{C}^{-1}$ (relating to the l-r-t system) may be used to express a linear elastic constitutive relation between stresses and strains as $$\overline{\sigma} = \overline{D}\overline{\epsilon} \quad (4)$$

where strain and stress components are stored in $\overline{\epsilon}$ and $\overline{\sigma}$, respectively, as $\overline{\epsilon}=[\epsilon_l\ \epsilon_r\ \epsilon_t\ \gamma_{lr}\ \gamma_{lt}\ \gamma_{rt}]^T$ and $\overline{\sigma}=[\sigma_l\ \sigma_r\ \sigma_t\ \tau_{lr}\ \tau_{lt}$ $\tau_{rt}]^T$. Strains and stresses may be transformed between the l-r-t system and the x-y-z system using a transformation matrix G as $$\overline{\epsilon}=G\epsilon \quad (5)$$

and $$\sigma=G^T\overline{\sigma} \quad (6)$$

respectively, where the transformation matrix $$G = \begin{bmatrix} a_l^x a_l^x & a_l^y a_l^y & a_l^z a_l^z & a_l^x a_l^y & a_l^z a_l^x & a_l^y a_l^z \\ a_r^x a_r^x & a_r^y a_r^y & a_r^z a_r^z & a_r^x a_r^y & a_r^z a_r^x & a_r^y a_r^z \\ a_t^x a_t^x & a_t^y a_t^y & a_t^z a_t^z & a_t^x a_t^y & a_t^z a_t^x & a_t^y a_t^z \\ 2a_l^x a_r^x & 2a_l^y a_r^y & 2a_l^z a_r^z & a_l^x a_r^y + a_l^y a_r^x & a_l^z a_r^x + a_l^x a_r^z & a_l^y a_r^z + a_l^z a_r^y \\ 2a_t^x a_l^x & 2a_t^y a_l^y & 2a_t^z a_l^z & a_t^x a_l^y + a_t^y a_l^x & a_t^x a_l^x + a_t^x a_l^z & a_t^y a_l^z + a_t^z a_l^y \\ 2a_r^x a_t^x & 2a_r^y a_t^y & 2a_r^z a_t^z & a_r^x a_t^y + a_r^y a_t^x & a_r^x a_t^x + a_r^x a_t^z & a_r^y a_t^z + a_r^z a_t^y \end{bmatrix} \quad (7)$$

is based on the components of A defined in Eq. (2). By premultiplication of Eq. (4) by $G^T$ and by considering Eqs. (5-6) it follows that the material matrix relating to the x-y-z system can be expressed as $$D=G^T\overline{D}G \quad (8)$$

Of particular interest for the following is that $c_{1,1}^{-1}$, i.e. the inverse of the component stored in the first row and first column of the compliance matrix $C=D^{-1}$, now is equal to $E_x(x,y,z)$, i.e. the local MOE valid in the longitudinal direction of the board. Knowing the material parameters and the relation between the l-r-t and x-y-z coordinate systems, a local MOE, for a given sub portion, i.e. a volume element, of the board in this longitudinal direction can thus be calculated.

Typical values for the wood material parameters, representative for Norway spruce, are given in the table below. These values are in the following termed nominal material parameters.

| | |
|---|---|
| $E_l$ | 10700 MPa |
| $E_r$ | 710 MPa |
| $E_t$ | 430 MPa |
| $G_{lr}$ | 500 MPa |
| $G_{lt}$ | 620 MPa |
| $G_{rt}$ | 24 MPa |
| $v_{lr}$ | 0.38 |
| $v_{lt}$ | 0.51 |
| $v_{rt}$ | 0.51 |

The surface fiber orientation data as illustrated in FIG. 2a can be used to estimate bending stiffnes in a board cross section (cf. 17 in FIG. 1), as will now be described with reference to FIGS. 5a and 5b. The cross section 17 in FIG. 5a extends in the y-z plane and FIG. 5b shows one corresponding flat surface along a length dx. The direction of the x-axis corresponds to the longitudinal direction 9 indicated in FIG. 1.

A bending stiffness across the y-axis can be determined, according to common beam theory, as $$EI_y = \iint E_x(z-\overline{z})^2 dy dz \quad (9)$$

where $E_x$ is the local MOE in the x direction and $z-\overline{z}$ indicates the distance to the neutral axis (a stiffness across the z-axis can be determined similarly).

As mentioned earlier, local MOE in the x direction, $E_x$, can be determined with knowledge of the relevant material parameters and the relation between the coordinate systems l-r-t and x-y-z. When a bending stiffness calculation is carried out based on the data illustrated in FIGS. 2a-2b, some assumptions and approximations are made.

First of all, it may be assumed that the diving angle of the fibres are zero, i.e. that the fibers are parallel with the recorded surface. Secondly, it may be assumed that t (direction tangential with annular ring and perpendicular with fiber direction) lies in the plane of the surface, i.e. in the xy-plane or in the xz-plane. This second assumption may be made as the mutual difference between $E_t$ and $E_r$ is very small as compared with either parameter's difference to $E_l$. Thirdly, the approximation is made that the fiber orientation in a sub-portion of the board, i.e. in a volume beneath the board surface, is parallel with the orientation at the surface. Thus, a board volume element 25, i.e. a sub-portion of the cross section along a length dx in the x-direction, has the same fibre angle φ as the one recorded at a corresponding surface section 27. Such a sub-portion may be defined for one recorded laser dot or a group of dots.

In the illustrated case, see FIG. 5a, the orientations at the short edge surfaces of the board are used as assumptions in a triangular (e.g. 45° base angles, base coinciding with edge) part of the cross section, tapering from the short edge surface, and the remaining part of the cross section is split between the flat surfaces. Other configurations are of course possible.

Based on these assumptions and the recorded data, the bending stiffness across the y-axis can be determined for a number of cross sections, each being based on a length of the board, dx, of e.g. 10 mm. This may produce an output graph as illustrated in FIG. 6, indicating a weak section 29 at the top end of the board.

The calculations carried out so far depend on the nominal material parameters being correct for each produced board. While this may be correct in some cases, and while the output nominal local x-direction MOEs may be useful in many applications, in reliable strength grading of wooden boards it is preferred to adjust the calculated data to compensate for material parameter deviations.

Even if wood of one specific species is graded, growth conditions (soil, water, sunlight, etc.) may affect the properties of the wood. More importantly, the board's location within the log may affect material parameters: usually stiffness is higher closer to the periphery, away from the pith.

It is possible to measure a global, average x-direction MOE for a board as a whole by applying an impact at the board end (in the x-direction) and measure the resulting resonance frequency, f. It is well known that:

$$E_{x,global} = 4 \cdot \rho \cdot f^2 \cdot L^2 \quad (10)$$

where ρ is the board density, f is the measured resonance frequency, and L is the board length. The density may be determined on the basis of either actual volume and actual weight of individual boards, or average density, determined for a certain moisture content, for the strength graded wood species.

Further, based on the aforementioned estimations of local MOEs, an estimated global MOE, $\hat{E}_{x, global}$ in the x-direction can be calculated by determining an average estimated local MOE over the entire board length.

By comparing $E_{x, global}$ and $\overline{E}_{x, global}$, a proportion between the real and estimated material parameters can be obtained. Based on this comparison, a better estimate of each local MOE in the board can thus be determined.

It should be noted that $E_{x, global}$ can be measured in other ways. For instance, the initially mentioned flatwise bending can be used as well. As the global MOE to a great extent depends on annual ring density and distance from the pith, another option is to carry out image analysis on the end surfaces where the annual rings are clearly visible. This analysis can provide a measure of annual ring density and distance from the pith that can be used e.g. as input to a lookup table which provides a global MOE as an output.

Figure 7:
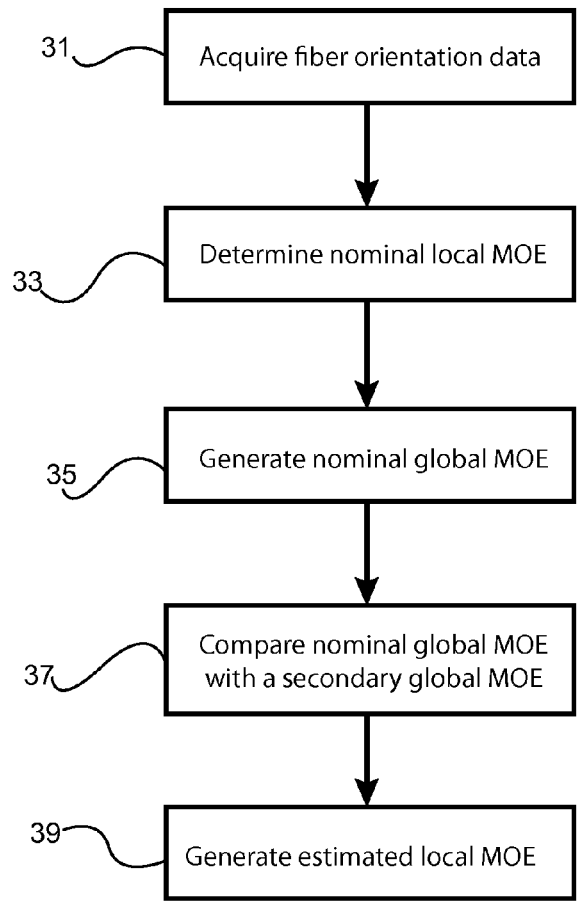
FIG. 7 shows a flow chart summarizing a method according to the disclosure.
Figure 8:
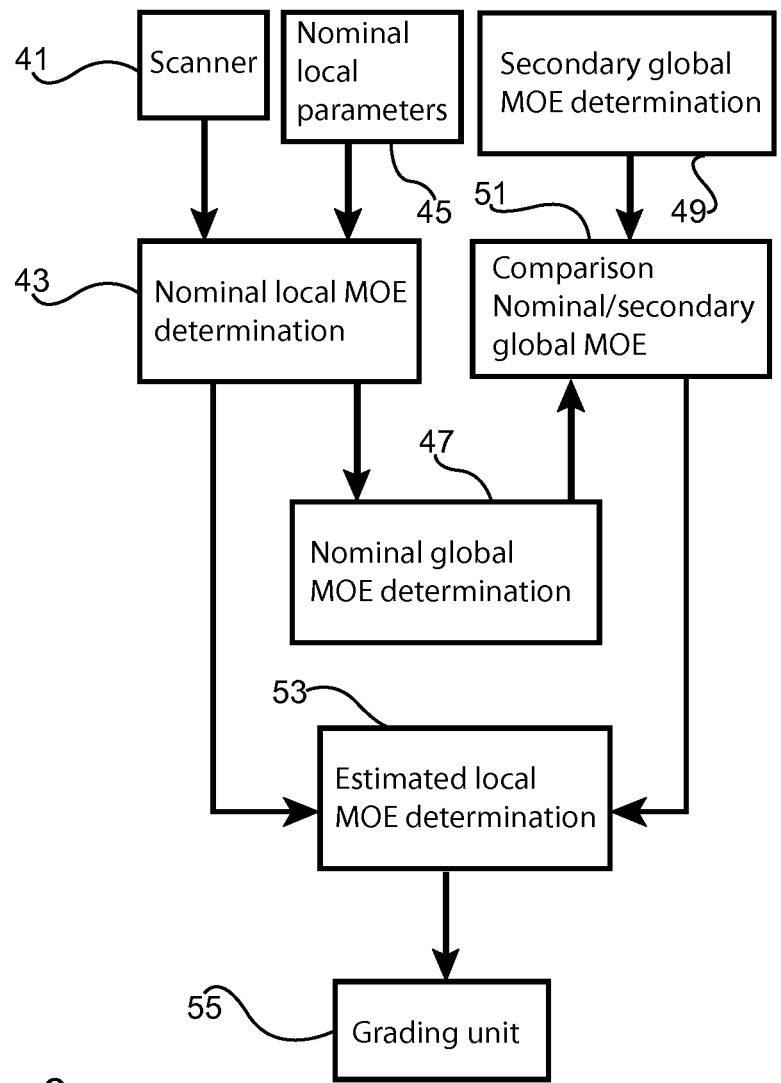
FIG. 8 illustrates blocks in an arrangement capable of carrying out the method.

To summarise, the method disclosed herein can be described with reference to the flow chart of FIG. 7, and a device for carrying out the method can at the same time be described with reference to FIG. 8. The device may include a scanner and various blocks for carrying out different calculations. Those blocks can be software-implemented, or more or less implemented with hardware.

To start with, data indicating fiber orientation over the surface of the board is acquired 31. This is done using a scanner 41 such as the WoodEye® system, although other options are possible as mentioned earlier.

Then, a nominal local x-direction MOE unit 43 determines 33 local MOEs as described earlier for a number of board sub-portions (e.g. 25 in FIG. 5a), based on the orientation data and nominal material parameters, fed from a memory 45.

Then, a nominal global MOE in the elongated direction for the wooden board as a whole is generated 35 based on the nominal local MOEs. This is done by a nominal global MOE unit 47.

A secondary global MOE is provided e.g. as mentioned by means of a resonance frequency sensing unit 49, and the secondary global MOE is compared 37, in a comparing unit 51, with the estimated nominal global MOE typically providing as an output a ratio between the two values.

Based on this comparison, the previously determined local x-direction MOEs are accordingly adjusted 39 in a local MOE estimator 53.

The estimated local MOEs are the outputs of the method. This output may be used e.g. as an input to a strength grading unit 55. The grading unit may then for instance calculate the cross section bending stiffness (across the y-axis, the way the board would be used as a beam) along the length of the board, as previously described. This provides output data similar to FIG. 6, now based on more exact MOEs, and the minimum cross section stiffness (or the minimum average cross section stiffness over a short distance along the board, a few centimeters or so) can be used as an indicating property, IP, for strength grading of the board in accordance with the lowest estimated bending stiffness along the length.

This IP provides excellent strength grading results. In an actual test carried out with 105 boards of Norway spruce with the dimensions 45×146×3600 mm, the coefficient of determination, $R^2$, between bending strength and minimum cross section stiffness (actually the minimum average cross section stiffness over a distance of 8 cm along the board) amounted to 0.68. As a comparison, strength grading based on global MOE determined only by measuring the lowest resonance frequency for each board for the same set of boards amounted to 0.59.

This means that using the IP based on minimum cross section bending stiffness as disclosed herein, the prediction of the load at which the board breaks deviates on average much less from the true load at which the board actually breaks. Using such a strength grading method it is therefore possible to grade more boards into higher classes while complying with standard requirements. Cross section axial stiffness could also be used.

The present disclosure is not restricted to the above described embodiments, and may be altered in various ways within the scope of the appended claims.

As used herein, the term board refers to any wooden member cut out from a log and having a main direction of extension.

The invention claimed is:

1. A method for evaluating a wooden board, the method comprising:
   acquiring data indicating fiber orientation for a surface of the wooden board;
   for each of a plurality of board sub-portions, determining a respective nominal local modulus of elasticity (MOE) associated with an elongated direction of the wooden board based on the fiber orientation and nominal material parameters $E_l$, $E_r$, $E_t$, $G_{lr}$, $G_{lt}$, $G_{rt}$, $v_{lr}$, $v_{lt}$, and $v_{rt}$, wherein the parameters $E_l$, $E_r$, $E_t$ indicate a moduli of elasticity in orthotropic directions of the wooden board, the parameters $G_{lr}$, $G_{lt}$, and $G_{rt}$ indicate a shear moduli in respective orthotropic planes of the wooden board, and the parameters $v_{lr}$, $v_{lt}$, and $v_{rt}$ are Poisson's ratios;
   generating a nominal global MOE associated with the elongated direction of the wooden board based on the determined nominal local MOEs;
   determining a secondary global MOE for the wooden board by exciting the wooden board with an impact in a longitudinal direction of the wooden board and measuring a primary resonance frequency of the wooden board;
   comparing the nominal global MOE with the secondary global MOE; and
   for each of the plurality of board sub-portions, determining a respective estimated local MOE associated with the elongated direction of the wooden board based on the fiber orientation and the comparison of the nominal global MOE with the secondary global MOE.

2. The method according to claim 1, wherein the data indicating fiber orientation over the surface of the wooden board is acquired using an optical scanner.

3. The method according to claim 1, wherein determining the respective nominal local MOE associated with the elongated direction of the wooden board for a given board sub-portion is performed based on an assumption that a volume of wood beneath the surface of the given board sub-portion has the same fiber orientation as the surface of the given board sub-portion.

4. The method according to claim 1, wherein the plurality of respective estimated local MOEs are used to determine a strength grade for the wooden board.

5. The method according to claim 4, wherein the strength grade is further based on an indicating property (IP).

6. The method according to claim 5, wherein the IP is based on a calculated bending stiffness in a number of cross sections along a length of the wooden board, and a minimum cross section bending stiffness is used as a basis for the IP.

7. The method according to claim 5, wherein the IP is based on a calculated axial stiffness in a number of cross sections along a length of the wooden board, and a minimum cross section axial stiffness being used as a basis for the IP.

8. The method according to claim 1, wherein the plurality of respective estimated local MOEs are used to determine a bending or an axial stiffness of the wooden board across a plurality of cross sections of a length of the wooden board.

9. A device comprising:
   a scanner configured to acquire data indicating fiber orientation for a surface of a wooden board; and
   a processing unit configured to:
      determine, for each of a plurality of board sub-portions, a respective nominal local modulus of elasticity (MOE) associated with an elongated direction of the wooden board based on the fiber orientation and nominal material parameters $E_l$, $E_r$, $E_t$, $G_{lr}$, $G_{lt}$, $G_{rt}$, $v_{lr}$, $v_{lt}$, and $v_{rt}$ wherein the parameters $E_l$, $E_r$, $E_t$ indicate a moduli of elasticity in orthotropic directions of the wooden board, the parameters $G_{lr}$, $G_{lt}$, and $G_{rt}$ indicate a shear moduli in respective orthotropic planes of the wooden board, and the parameters $v_{lr}$, $v_{lt}$, and $v_{rt}$ are Poisson's ratios, and generate a nominal global MOE associated with the elongated direction of the wooden board based on the determined nominal local MOEs; and a resonance frequency sensing unit configured to:
determine a secondary global MOE for the wooden board by exciting the wooden board with an impact in a longitudinal direction of the wooden board, and measure a primary resonance frequency of the wooden board, wherein the processing unit is further configured to compare the nominal global MOE with the secondary global MOE, and wherein the processing unit is further configured to determine, for each of the plurality of board sub-portions, a respective estimated local MOE associated with the elongated direction of the wooden board based on the fiber orientation and the comparison of the nominal global MOE with the secondary global MOE.

10. The device according to claim 9, wherein the processing unit is further configured to determine a strength grade for the wooden board based on the plurality of respective estimated local MOEs.

11. The device according to claim 10, wherein the strength grade is further based on an indicating property (IP).

12. The device according to claim 11, wherein the IP is based on a calculated bending stiffness in a number of cross sections along a length of the wooden board, and a minimum cross section bending stiffness is used as a basis for the IP.

13. The device according to claim 9, wherein the processing unit is configured to determine the respective nominal local MOE associated with the elongated direction of the wooden board for a given board sub-portion based on an assumption that a volume of wood beneath the surface of the given board sub-portion has the same fiber orientation as the surface of the given board sub-portion.

14. A method comprising:
acquiring data indicating fiber orientation for a surface of a wooden board;

for each of a plurality of board sub-portions, determining a respective estimated nominal local modulus of elasticity (MOE) associated with an elongated direction of the wooden board based on the fiber orientation and nominal material parameters $E_l$, $E_r$, $E_t$, $G_{lr}$, $G_{lt}$, $G_{rt}$, $v_{lr}$, $v_{lt}$, and $v_{rt}$, wherein the parameters $E_l$, $E_r$, $E_t$ indicate a moduli of elasticity in orthotropic directions of the wooden board, the parameters $G_{lr}$, $G_{lt}$, and $G_{rt}$ indicate a shear moduli in respective orthotropic planes of the wooden board, and the parameters $v_{lr}$, $v_{lt}$, and $v_{rt}$ are Poisson's ratios;

generating a nominal global MOE associated with the elongated direction of the wooden board based on the determined nominal local MOEs;

determining a secondary global MOE for the wooden board by exciting the wooden board with an impact in a longitudinal direction of the wooden board and measuring a primary resonance frequency of the wooden board after excitation; and for each of the plurality of board sub-portions, determining a respective estimated local MOE associated with the elongated direction of the wooden board based on the fiber orientation, the nominal global MOE, and the secondary global MOE.

15. The method according to claim 14, further comprising:
comparing the nominal global MOE with the secondary global MOE.

16. The method according to claim 15, wherein determining the respective estimated local MOEs for each of the plurality of board sub-portions is based on the comparison of the nominal global MOE with the secondary global MOE.

17. The method according to claim 14, wherein determining the respective nominal local MOE associated with the elongated direction of the wooden board for a given board sub-portion is performed based on an assumption that a volume of wood beneath the surface of the given board sub-portion has the same fiber orientation as the surface of the given board sub-portion.

* * * * *